(12) United States Patent
Chilkoti et al.

(10) Patent No.: US 6,444,254 B1
(45) Date of Patent: Sep. 3, 2002

(54) MICROSTAMPING ACTIVATED POLYMER SURFACES

(75) Inventors: Ashutosh Chilkoti, Durham, NC (US); Zhongping Yang, Woodbury, MN (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/519,038

(22) Filed: Mar. 3, 2000

(51) Int. Cl.[7] ............................. B05D 1/28; B05D 3/10; B05D 5/04

(52) U.S. Cl. .................... 427/2.24; 427/2.25; 427/2.28; 427/2.3; 427/2.31; 427/400; 427/460; 427/461; 427/466; 427/469; 427/487; 427/488; 427/510; 427/511; 427/533; 427/535; 427/536; 427/552; 427/554; 427/555; 427/258; 427/261; 427/414; 427/429; 216/58; 216/63; 216/67

(58) Field of Search ............................... 427/400, 2.24, 427/2.25, 2.28, 2.3, 2.31, 460, 461, 466, 469, 487–488, 510–511, 533, 535–536, 552, 554–555, 256, 261, 414, 429; 118/264; 216/58, 63, 67

(56) References Cited

U.S. PATENT DOCUMENTS

| | | | |
|---|---|---|---|
| 4,282,287 A | * 8/1981 | Giese | 428/407 |
| 4,737,544 A | * 4/1988 | McCain et al. | 525/54.1 |
| 5,055,316 A | 10/1991 | Hoffman et al. | 427/2 |
| 5,512,131 A | * 4/1996 | Kumar et al. | 156/655.1 |
| 5,607,475 A | 3/1997 | Cahalan et al. | 623/11 |
| 5,609,907 A | * 3/1997 | Natan | 427/2.12 |
| 5,620,850 A | 4/1997 | Bamdad et al. | 530/300 |
| 5,645,883 A | * 7/1997 | Russell et al. | 427/2.25 |
| 5,725,788 A | 3/1998 | Maracas et al. | 216/41 |
| 5,776,748 A | 7/1998 | Singhvi et al. | 435/180 |
| 5,817,242 A | 10/1998 | Biebuyck et al. | 216/41 |
| 5,866,113 A | * 2/1999 | Hendriks et al. | 424/78.17 |
| 5,891,506 A | * 4/1999 | Keogh | 427/2.13 |
| 5,900,160 A | 5/1999 | Whitesides et al. | 216/41 |
| 5,925,259 A | 7/1999 | Biebuyck et al. | 216/2 |
| 5,962,136 A | 10/1999 | Dewez et al. | 428/410 |
| 5,976,826 A | 11/1999 | Singhvi et al. | 435/29 |
| 5,998,588 A | 12/1999 | Hoffman et al. | 530/402 |
| 6,027,890 A | * 2/2000 | Ness et al. | 435/6 |
| 6,033,719 A | * 3/2000 | Keogh | 427/2.12 |
| 6,048,735 A | * 4/2000 | Hessel et al. | 436/518 |
| 6,060,121 A | * 5/2000 | Hidber et al. | 427/261 |
| 6,089,853 A | * 7/2000 | Biebuyck et al. | 425/447 |
| 6,096,386 A | * 8/2000 | Biebuyck et al. | 427/510 |
| 6,165,566 A | * 12/2000 | Tropsha | 427/536 |

FOREIGN PATENT DOCUMENTS

WO      WO 98/58967      12/1998      ........... C07K/17/14

OTHER PUBLICATIONS

Ghosh, Pradyut et al., Covalent Grafting of a Patterned, Hyperbranched Polymer onto a Plastic Substrate Using Microcontact Printing, J. Am. Chem. Soc. 1999, 121, 8395–8396.*

Blawas et al.; "Protein Patterning" *Biomaterials* 19 595–609 (1998).

International Search Report for PCT/US01/06547, Date of Mailing Feb. 1, 2002.

(List continued on next page.)

Primary Examiner—Shrive P. Beck
Assistant Examiner—Jennifer Kolb Michener
(74) Attorney, Agent, or Firm—Myers Bigel Sibley & Sajovec

(57) ABSTRACT

Functionalized polymer surfaces having reactive moieties thereon are contacted with stamps having ligands adsorbed thereto, the ligands also comprising reactive moieties. The reactive moieties of the functionalized surfaces and the ligands form covalent bonds, thus providing a method of microstamping polymer surfaces directly with ligands such as biological ligands. Using this method, devices such as tissue culture plates with polymer surfaces that are microstamped directly with ligands can be made.

32 Claims, 9 Drawing Sheets

OTHER PUBLICATIONS

Blawas, A.S.; Reichert, W. M. *Biomaterials* 1998 19, 595.

Mrksich, M.; Whitesides, G. M. *TIBTECH* 1995, 13, 228.

Kumar, A.; Abbott, N.; Kim, E.; Biebuyck, H.; Whitesides. G. M. *Acc. Chem. Res.* 1995, 28, 219.

Xia, Y.; Whitesides, G. M. *Angew. Chem. Int. Ed. Engl.* 1998, 37, 550.

Lahiri, J.; Ostuni, E.; Whitesides, G. M. *Langmuir* 1999, 15, 2055.

Bernard, A.; Delamarche, E.; Schmid, H.; Michel, B.; Bosshard, H. R.; Biebuyck, H. *Langmuir* 1998, 14, 2225.

Shakesheff, K.; Cannizzaro, S.; Langer, R. *J. Biomater. Sci., Polym. Ed.* 1998, 9, 507.

Cima, L.G. *J. Cell. Biochem.* 1994, 56, 155.

Massia, S. P.; Hubbell, J. A. *J. Biomed. Mater. Res.* 1991, 25, 223.

Brandley, B. K.; Schnaar, R. L. *Anal. Biochem.* 1988, 172, 270.

Massia, S. P.; Hubbell, J. A. *Anal. Biochem.* 1990, 187, 292.

Mooney, J. F.; Hunt, A. J.; McIntosh, J. R.; Librerko. C. A..; Walba, D. M.; Rogers, C. T. *Proc. Natl. Acad. Sci. (USA)* 1996, 93, 12287.

Wybourne, M. N.; Yan, M.; Keana, J. K. W.; Wu, J. C. *Nanotechnology* 1996, 7, 302.

Hengsakul, M.; Cass, A. E. G. *Bioconj. Chem.* 1996, 7, 249.

Schwarz, A.; Rossier, J. S.; Roulet, E.; Mermod, N.; Roberts, M. A.; Girault, H. H. *Langmuir* 1998, 14, 5526.

Dewez, J.–L.; Lhoest, J.–B.; Detrait, E.; Berger, V.; Dupont––Gillain, C. C.; Vincent, L.–M.; Schneider, Y.–J.; Bertrand, P.; Rouxhet, P. G. *Biomaterials* 1998, 19.

Chen, C.S.; Mrksich, M.; Huang, S.; Whitesides, G. M.; Ingber, D.E. *Science* 1997, 276, 1425.

Mrksich, M.; Dike, L.E.; Tien, J.; Ingber, D.E.; Whitesides, G. M. *Exp. Cell Res.* 1997, 235,305.

Chen, C. S; Mrksich, M.; Huang, S.; Whitesides, G. M.; Ingber D.E *Biotechnol. Prog.* 1998, 14, 356.

Ghosh, P.; Crooks, R.M. *J. Am. Chem. Soc.,* 1999, 121, 8395.

Massia, S.P.; Hubbell, J. A. *Ann. N.Y. Acad. Sci.–Biomed. Engr.* 1990, 589, 261.

Lofas, S.; Johnsson., B. *J. Chem. Soc., Chem. Commun.* 1990, 1526.

Adamczyk, M.; Fishpaugh, J. R.; Mattingly, P. G. *Tetrahedron Lett.* 1995, 36, 8345.

Kovacs, J.; Mayers, G. L.; Johnson, R. H.; Cover, R. E.; Ghatak, U.R. *J. Org. Chem.* 1970, 35, 1810.

Wilbur, J. L.; Kumar, A.; Kim, E.; Whitesides, G. M. *Adv. Mater.* 1994, 6, 600.

Hermanson, G.T. Bioconjugate Techniques, Academic Press, 1$^{st}$ Ed., San Diego, 1996.

Chilkoti, A.; Tan, P. H.; Stayton, P. S *Proc. Natl. Acad. Sci., USA* 1995, 92, 1754.

Chilkoti, A.; Stayton, P. S. *J. Am. Chem. Soc.* 1995, 117, 10622.

Kumar, D. J.; Srivastava, H. C. *J. Appl. Polym. Sci.* 1987, 33, 455.

Solbrig, C. M., Obendorf, S. K. *J. Appl. Polym. Sci.: Appl. Polym. Symp.* 1991, 47, 437.

Búi, L. N., Thompson, M., McKeown, N. B.; Romaschin, A. D.; Kalman, P. G. *Analyst.* 1993, 118, 463.

Chen, W.; McCarthy, T. J. *Langmuir* 1998, 14, 5586.

Yao, Z. P.; Rånby, B. *J. Appl. Polym. Sci.* 1990, 41, 1459.

Avny, Y.; Reubenfeld, L. *J. Appl. Polym. Sci.* 1986, 32, 4009.

Desai, N. P., Hubbell, J. A. *Macromolecules* 1992, 25, 226.

Mougenot, P.; Marchand–Brynaert, J. *Macromolecules* 1996, 29, 3552.

Mougenot, P.; Koch, M.; Dupont, I.; Schneider, Y.–J.; Marchand–Brynaert, J. *J. Coll. Interfac. Anal.* 1996, 177, 162.

Wang, J.; Feng, D.; Wang, H.; Rembold, M.; Fritz, T. *J. Appl. Polymer, Sci.,* 1993, 50, 585.

Bertrand, P.; DePuydt, Y.; Beuken, J. M.; Lutgen, P.; Feyder, G. *Nucl. Meth. Phys. Res., Sect. B.* 1987, 19–20, 887.

Arenolz, E.; Heitz, J.; Waghner, M.; Bauerle, D.; Hibst, H.; Hagemeyer, A. *Appl. Surf. Sci.* 1993, 69, 16.

Ratner, B. D.; Chilkoti, A.; Lopez, G. P. In *Plasma deposition, treatment, and etching of polymers;* D'Agostino, Ed.; Academic Press, Inc.: New York, 1990.

Whitesides, G.M. Wet Chemical Approaches to the Characterization of Organic Surfaces: Self–Assembled Monolayers, Wetting, and the Physical–Organic Chemistry of the Solid–Liquid Interface, *Langmuir* 6, 87–96 (1990).

* cited by examiner

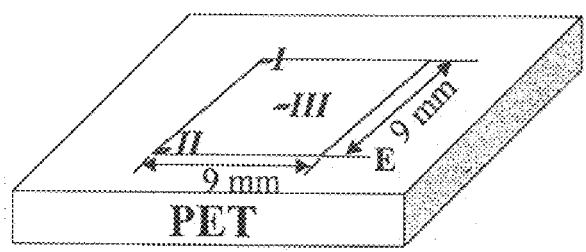
FIG. 4A.
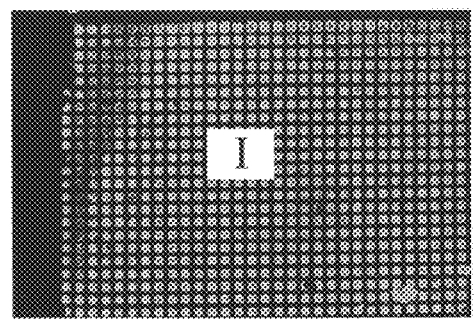
FIG. 4B.
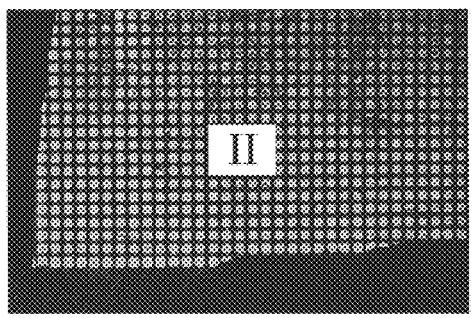
FIG. 4C.
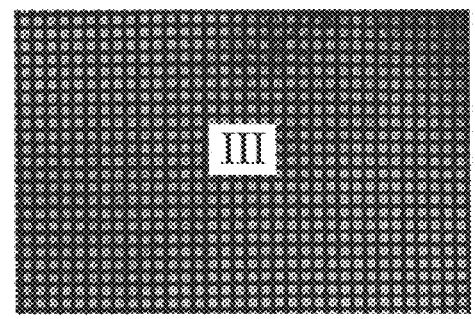
FIG. 4D. 100 μm

MICROSTAMPING ACTIVATED POLYMER SURFACES

FIELD OF THE INVENTION

This invention relates to microcontact printing (i.e., microstamping) of biomolecules and other ligands onto polymer surfaces.

BACKGROUND OF THE INVENTION

Micropatterning of biomolecules on surfaces has a number of applications, including the modulation of cell-substrate interactions in biomaterials and tissue engineering and the fabrication of multi-analyte biosensors and genomic arrays. See Blawas, A. S. et al, *Biomaterials* (1998), 19, 595; Mrksich, M. and Whitesides, G. M., *TIBTECH* (1995) 13, 228. Microcontact printing (also referred to herein as "$\mu$CP") methods are attractive for micropatterning of biomolecules, because of their simplicity and ease of use. See Kumar, A. et al., *Acc. Chem. Res.* 1995, 28, 219; Xia, Y. et al., *Angew. Chem. Int. Ed. Engl.* (1998), 37, 550. To date, however, methods of microstamping have generally been limited to the production of patterns on self assembling monolayers (SAMs), which in turn are bound to gold or silicon surfaces. For example, Whitesides and coworkers have used reactive $\mu$CP to pattern biological ligands onto reactive SAMs on gold. J. Lahiri, et al., *Langmuir* 1999, 15, 2055. Bernard et al. have similarly used $\mu$CP to pattern different proteins onto SAMs on gold by physical adsorption. See Bernard, A.; et al., *Langmuir* 1998, 14, 2225.

U.S. Pat. No. 5,512,131 to Kumar et al. describes a method of patterning a surface in which an elastomeric stamp with a stamping surface is coated with a self-assembled monolayer-forming species having a functional group selected to bind to surface. The stamp is then placed against the surface to leave a self-assembled monolayer of the species originally coated onto the stamp. The description of the invention is, however, limited to the use of self-assembling monolayers. While SAMs are commonly used, the limitation of being required to use them is disadvantageous in that SAMs generally bind only to certain materials such as metals (usually gold), silicon dioxide, gallium arsenide, glass, and the like. The patent fails to provide any example of a non-SAM species being used to bind directly to a surface, nor does the patent recite any examples of microstamping onto a material other than gold.

While SAMs on gold are generally used for micropatterning, they have limited utility as biomaterials. In contrast, polymers are widely used as biomaterials. (Zdrahala, R. J., *J. Biomater. Appl.* (1996) 10, 309). Most previous studies on micropatterning on polymers have utilized photolithography. (Mooney, J. F. et al., *Proc. Natl. Acad. Sci.* (*USA*) 1996, 93, 12287. Wybourne, M. N. et al., *Nanotechnology* 1996, 7, 302. Hengsakul, M et al., *Bioconj. Chem.* 1996, 7, 249. Schwarz, A. et al., *Langmuir* 1998, 14, 552; Dewez, J.-L. et al., *Biomaterials* 1998, 19). Alternative methods have also been demonstrated by Ghosh and Crooks, who patterned hyperbranched poly(acrylic acid) on oxidized poly(ethylene) using reactive $\mu$CP. (Ghosh, P.; Crooks, R. M. *J. Am. Chem. Soc.*, 1999,121, 8395).

The micropatterning of biological molecules onto surfaces is an important objective because such patterning enables, for example, control of cell-substrate interactions. (Chen, C. S.; et al., *Science* 1997, 276, 1425. Mrksich, M. et al., *Exp. Cell Res.* 1997, 235, 305. Chen, C. S; et al., Whitesides, G. M. et al., *Biotechnol. Prog.* 1998, 14, 356). In the last decade, biomolecules have been immobilized onto the surface of different polymers in order to modulate their interaction with cells. (Shakesheff, K. et al., *J. Biomater. Sci., Polym. Ed.* 1998, 9, 507; Cima, L. G., *J. Cell. Biochem.* 1994, 56, 155; Massia, S. P. et al., *J. Biomed. Mater. Res.* 1991, 25, 223; Brandley, B. K.; et al., *Anal. Biochem.* 1988, 172, 270. Massia, S. P. et al., *Anal. Biochem.* 1990, 187, 292). More recent studies have focused on patterning polymer surfaces with biological ligands. Mooney, J. F.; Hunt, et al., *Proc. Natl. Acad. Sci.* (*USA*) 1996, 93, 12287. Wybourne, M. N. et al., *Nanotechnology* 1996, 7, 302; Hengsakul, M. et al., *Bioconj. Chem.* 1996, 7, 249; Schwarz, A.; et al., *Langmuir* 1998, 14, 5526; Dewez, J.-L. et al., P. G. *Biomaterials* 1998, 19).

Despite the foregoing, current attempts to micropattern biological ligands onto polymer surfaces are severely limited. Most $\mu$CP methods are done and indeed are required to be performed on gold or similar metal surfaces. Typically, a SAM-molecule is stamped onto a gold surface to create a patterned SAM layer on the gold surface. See Kumar, A. et al., supra. In a modification of this basic method, Lahiri et al., supra, have developed a method in which a homogeneous SAM is formed on gold by incubating the gold surface in a solution of the SAM-forming molecules. Next, a stamp is used to transfer a non-SAM reactive molecule to the SAM/gold surface. The reactive molecule reacts with a with a reactive molecule in the SAM to form a pattern of the reactive molecule on the SAM/gold surface. These methods are limiting because they are restricted to the use of gold or other SAM forming surfaces, and require the use of SAM-forming molecules. These approaches are not applicable to polymer surfaces because SAMs do not generally form on polymers. In yet another alternative approach (Barnard et al., supra), a stamp "inked" with protein is used to stamp a pattern of the protein onto a polymer. A significant limitation of this method is that the protein is not bound to the polymer surface via a stable, covalent linkage or bond. Rather, the protein is attached to the polymer surface by physical adsorption. This approach is limiting because many molecules of interest cannot be stably bound to polymer surfaces by non-specific physical adsorption, and the patterned molecule is easily removed from the polymer surface by water, buffers, biological fluids and the like.

Thus, the successful patterning of biological ligands directly onto polymer surfaces using reactive microstamping techniques (i.e., in which reactions between the ligands and the polymer surfaces occur to create a stable covalent bond between the two) has heretofore remained elusive. Accordingly, a need exists for a reliable method of microstamping biological and other ligands directly and covalently onto polymer surfaces.

SUMMARY OF THE INVENTION

The present inventor has discovered a novel methodology of reactive $\mu$CP microstamping that overcomes many of the shortcomings presented by the present available methods. This methodology enables biological ligands and proteins to be directly patterned on polymers with a spatial resolution of at least 5 $\mu$m and good reproducibility. In addition to providing a desirable level of resolution, the methods of the present invention also provide spatial control of ligand presentation on the surface of commonly used polymeric biomaterials.

Accordingly, a first aspect of the present invention is a method of microstamping a polymer surface with a ligand, in which a functionalized polymer surface having a reactive moiety thereon is contacted with a stamp adsorbed onto its surface at least one ligand comprising a second reactive moiety, wherein the second reactive moiety of the ligand and the first reactive moiety of the polymer surface form a covalent bond. After the covalent bond is formed, the stamp is separated from the functionalized polymer surface, thereby leaving the ligand covalently bound to the functionalized polymer surface.

This method results in spatially-resolved transfer and coupling of the ligand to the reactive surface of the polymer. In a preferred embodiment of the invention, the ligand is a biological ligand. However, other ligands, including synthetic polymers, may also be used in the methods of the present invention.

An additional aspect of the invention is a device comprising at least one microstamped polymer surface, wherein the polymer surface is covalently bound to at least one ligand. Methods of forming such devices, such as tissue culture plates, are also an aspect of the invention.

The foregoing and other aspects of the present invention are explained in detail in the specification set forth below.

BRIEF DESCRIPTION OF THE DRAWINGS

FIG. 4 illustrates 10×magnification confocal images of Alexa™ 488 labeled streptavidin patterns from a 9 mm×9 mm area, patterned with biotin-amine on PET-COOH by MAPS. A PDMS stamp with 10 $\mu$m square feature and an interfeature spacing of 5 $\mu$m was used to generate these patterns. A is a schematic of the patterned area, showing the location of regions from which the fluorescence images in panels B, C and D were taken.

DETAILED DESCRIPTION OF THE PREFERRED EMBODIMENTS

Figure 1:
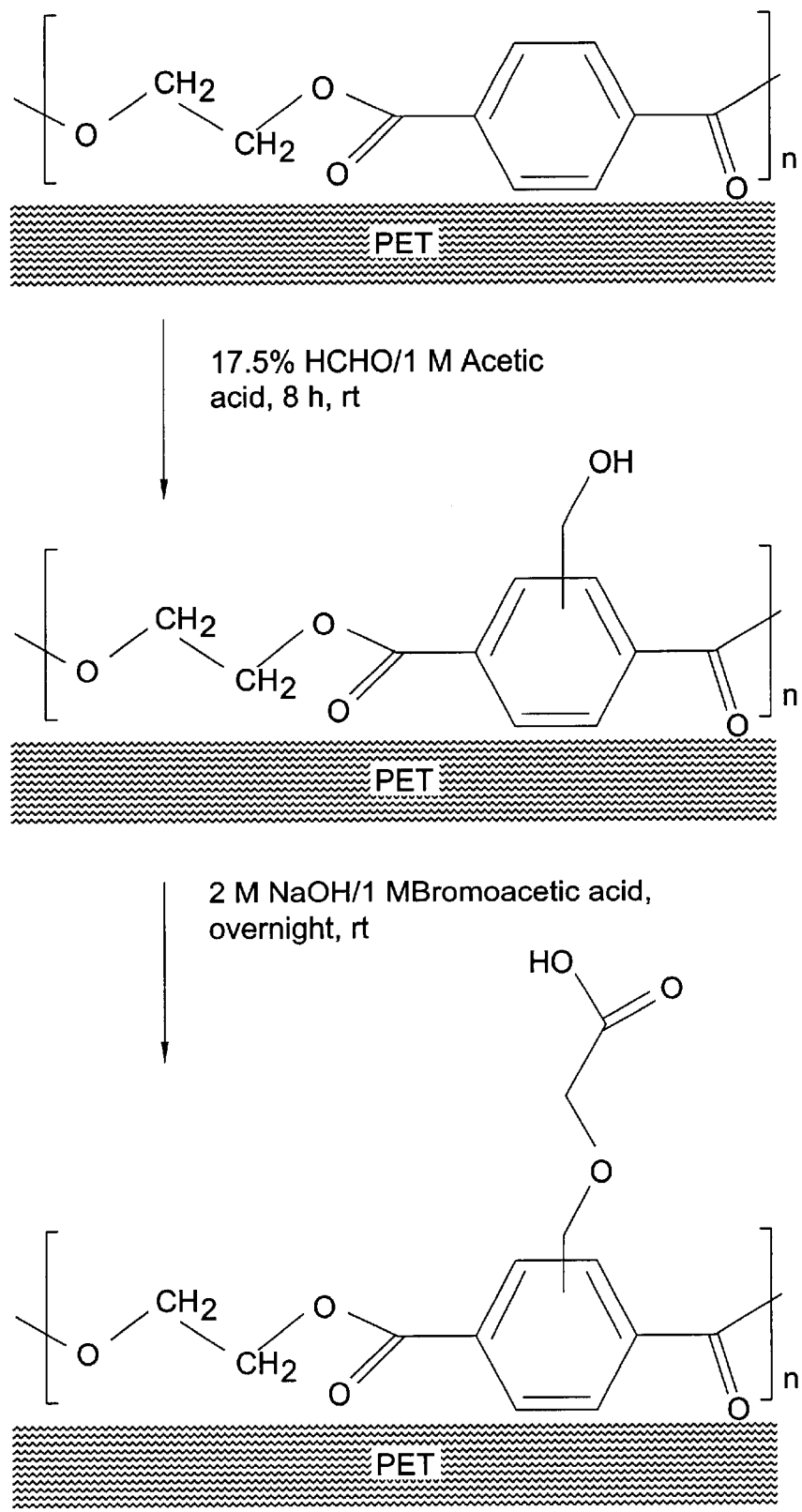
FIG. 1 is a schematic of surface chemical derivatization to introduce carboxylic acid groups in PET.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The methods described in the present invention are sometimes referred to herein by the acronym "MAPS," an abbreviation for Microstamping onto an Activated Polymer Surface. The method involves functionalized polymer surfaces having reactive moieties (also referred to as "reactive groups" or "functional groups" herein) on the surface of the polymer. The functionalized polymer surface is contacted with a stamp having on its surface ligands comprising reactive moieties that react with the reactive moieties on the polymer surface to produce a covalent bond.

Polymers useful in the present invention may be natural polymers (e.g., biological polymers) or synthetic polymers. Synthetic polymers that may be used in the present invention include but are not limited to known synthetic polymers such as poly(ethylene terephthalate) (PET), polystyrene (PS), polycarbonate (PC), poly(epsilon-caprolactone)

(PECL or PCL), poly(methyl methacrylate) (PMMA), poly (lactic acid) (PLA), polydimethylsiloxane (PDMS), polybutadiene (PB), polyvinylalcohol (PVA), fluorinated polyacrylate (PFOA), poly(ethylene-butylene) (PEB), and poly(styrene-acrylonitrile) (SAN). Polymers according to the present invention also encompass biological polymers, such as peptides, proteins, and repeating units of nucleic acid (i.e., DNA and RNA). In any event, the term "polymer" will be defined herein as a compound or molecule comprising at least two units of a monomer or repeating unit, as these terms are understood in the art.

The term "polymer" as used herein is also intended to encompass a homopolymer, heteropolymer, co-polymer, terpolymer, etc., and blends, combinations and mixtures thereof.

Polymer surfaces of the present invention are preferably flat or planar, but may be also be curved, cylindrical, or shaped according to the user's needs. For example, the polymer surface may also be corrugated, rugose, concave, convex or any combination of these conformations. The polymer surface may be a film or sheet of polymer, a strand, a tubing, a sphere, a container, a capillary, a pad, a molded plastic device, or a plastic plate (i.e., a tissue culture plate). The polymer surface may be on prosthetic or implantable device on which it is desired to covalently bond certain ligands, and which ligands may be capable of binding or attracting other compounds or biological matter (e.g., cells, proteins, or other biological materials).

The functionalized polymer surface of the invention (also referred to herein as the "substrate") will have at least one reactive moiety on its surface. The polymer surface may be functionalized by means known in the art to produce reactive moieties on the surface of the polymer. Reactive moieties include but are not limited to amine groups, sulfur-containing functional groups such as thiols, sulfides, disulfides, and the like; silanes and chlorosilanes; carboxylic acids; nitrites and isonitriles; and hydroxamic acids. Additional suitable reactive moieties include acid chlorides, anhydrides, sulfonyl groups, phosphoryl groups, azo, diazo and hydroxyl groups. Presently, —COOH or carboxylic acid groups are preferred. Exemplary reactive moieties may be hydrophobic, hydrophilic, amphipathic, ionic, nonionic, polar, nonpolar, halogenated, alkyl, or aryl. A non-limiting, exemplary list of such reactive moieties includes: —OH, —CONH—, —CONHCO—, —NH$_2$, —NH—, —COOH, —COOR, —CSNH—, —NO$_2^-$, —SO$_2^-$, —RCOR—, —RCSR—, —RSR, —ROR—, —PO$_4^{-3}$, —OSO$_3^{-2}$, —SO$_3^-$, —NH$_x$R$_{4-x+}$, —COO$^-$, —SOO$^-$, —RSOR—, —CONR$_2$, —(OCH$_2$CH$_2$)$_n$OH (where n=1–20, preferably 1–8), —CH$_3$, —PO$_3$H$^-$, —2-imidazole, —N(CH$_3$)$_2$, —NR$_2$, —PO$_3$H$_2$, —CN, —(CF$_2$)$_n$CF$_3$ (where n=1–20, preferably 1–8), olefins, and the like. In this list, R may hydrogen or an organic group such as a hydrocarbon or fluorinated hydrocarbon. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups. Alternatively, R may be a biologically active species such as an antigen, antibody, hapten, etc. Additional reactive moieties suitable for use in the present invention may also be found in U.S. Pat. No. 5,079,600, issued Jan. 7, 1992, and incorporated herein by reference.

Functionalization, as used herein, means a method comprising one or more steps in which a reactive moiety is introduced onto the surface of the polymer.

Functionalization may occur in one, two, or even more steps, with each step generally being a chemical or thermal modification a polymer surface, the end result of which is a surface onto which a reactive group is introduced. For example, when the polymer surface is PET, the PET surface may first be hydroxylated, and then reacted with one or more compounds as known in the art to introduce carboxylic acid moieties onto the surface. The carboxylic acids may then be activated (i.e., using pentaflurophenol) in order to make the carboxylic acid group moieties reactive with other reactive moieties. Several methods of introducing reactive groups onto the surface of polymers are known, including hydrolysis (Kumar, D. J.; Srivastava, H. C. *J. Appl. Polym. Sci.* 1987, 33, 455.; Solbrig, C. M. et al., *J. Appl. Polym. Sci.: Appl. Polym. Symp.* 1991, 47, 437; Bui, L. N., et al. *Analyst.* 1993, 118, 463) and reduction (Bui, L. N. et al., *Analyst.* 1993, 118, 463; Chen, W. et al., *Langmuir* 1998, 14, 5586). Other chemical approaches that can also be used to introduce reactive groups onto the surface of the polymer are photoinitiated graft polymerization, (Yao, Z. P.; et al., *J. Appl. Polym. Sci.* 1990, 41, 1459) aminolysis, (Avny, Y. et al., J. Appl. Polym. Sci. 1986, 32, 4009), the formation of a surface interpenetrating network of poly(ethylene oxide), (Desai, N. P. et al., *Macromolecules* 1992, 25, 226), chemical reaction at hydroxyl end-groups (Mougenot, P. et al., *J. Macromolecules* 1996, 29, 3552; Mougenot, P.; et al., *J. Coll. Interfac. Anal.* 1996, 177, 162), corona discharge, (Strobel, M. et al., *J. Adhes. Sci. Technol.* 1992, 5, 429), reactive plasma etching, (Wang, J. et al.,*J. Appl. Polym. Sci.*, 1993, 50, 585), laser treatment (Bertrand, P. et al., *Nucl. Meth. Phys. Res., Sect. B.* 1987, 19–20, 887) and ion beam modification. (Arenolz, E. et al., *Appl. Surf. Sci.* 1993, 69, 16; Ratner, B. D. et al., in *Plasma Deposition, Treatment, and Etching of Polymers* (D'Agostino, Ed.; Academic Press, Inc.: New York, 1990).

In the present invention, the functionalized surface of the polymer having a reactive moiety thereon is contacted with a stamp comprising on its surface a ligand comprising a reactive moieties. Reactive moieties of the ligand may be any of the reactive moieties set forth above, as long as they are able to covalently bind to the functionalized polymer surface.

Stamps useful in the present invention are known in the art and may be commercially available. Generally, these stamps are produced by casting a polymeric material onto a mold having the desired pattern. The particular material chosen for formation of the stamp is not critical to the present invention, but should be chosen so as to satisfy certain physical characteristics. In a preferred embodiment, the stamp is elastomeric. Polymeric materials suitable for use in the fabrication of the stamp may have linear or branched backbones, and may be crosslinked or non-crosslinked, depending upon the particular polymer and the degree of formability desired of the stamp. A variety of elastomeric polymeric materials are suitable for such fabrication, especially polymers of the general classes of silicone polymers and epoxy polymers, with silicone elastic polymers being preferred. Examples of silicone elastomers suitable for use as the stamp include those formed from precursors including the chlorosilanes such as methylchlorosilanes, ethylchlorosilanes, and phenylchlorosilanes, and the like. A particularly preferred silicone elastomer is polydimethylsiloxane (PDMS).

The stamp should also be formed such that the stamping surface comprises a material that ligands of the present invention may adsorb to. The invention may be carried out using stamps as described in U.S. Pat. No. 5,817,242 to Biebuyck et al., the disclosure of which is incorporated herein in its entirety. In a particularly preferred embodiment, the stamp is oxidized, and more preferably is plasma-oxidized, prior to contact with the polymer surface.

The term "ligand," as used herein, means any molecule or compound capable of forming a covalent bond with another reactive molecule or compound. Stated another way, a ligand is a molecule that will covalently bind to a complementary site on another structure or compound. The site of binding may be the reactive moiety of another compound, i.e., a polymer. The ligands of the present invention accordingly comprise at least one reactive moiety (also referred to herein as a "reactive group"). The reactive moiety of the ligand may be at the physical terminus of the ligand, or at any site on the ligand available for forming a covalent bond. Reactive moieties will vary according to the particular ligand being used and the reactive group on the functionalized surface of the polymer to which the ligand will covalently bind. Stated another way, a ligand will comprise a reactive moiety compatible with the ligand and capable of binding to the reactive moiety on the surface of the functionalized polymer surface, such that the reactive moiety of the ligand and the reactive moiety of the polymer surface form a covalent bond. Reactive moieties of the present invention may be any one of the reactive moieties listed above as possible reactive moieties for the functionalized polymer surface, with amine groups being presently preferred. Ligands may naturally comprise reactive moieties, or reactive moieties may be attached or bound to the ligand in some way.

In one embodiment of the invention, the reactive moiety is connected to the ligand by means of a spacer molecule. The spacer may be polar; non-polar; halogenated or, in particular, fluorinated; positively charged; negatively charged; or uncharged. For example, a saturated or unsaturated, linear or branched alkyl, aryl, or other hydrocarbon spacer may be used. In one embodiment of the invention, the spacer is polyethylene glycol; in another embodiment, the spacer is an ethylene glycol oligomer.

The ligands of the present invention are generally attached to the stamp by adsorption, which adsorption techniques are known in the art.

Ligands are preferably biological ligands, although non-biological ligands such as synthetic polymers that are naturally reactive or functionalized to be reactive with other reactive groups or functional groups are also encompassed by this term. Biological ligands of the present invention include but are not limited to proteins, peptides, nucleic acids, carbohydrates, lipids, polysaccharides, and other biological molecules. Biological molecules may include, for example, biotin, vitamins, cofactors, coenzymes, receptor agonists or antagonists, etc. The biological ligand may selectively bind various biological or other chemical species such as proteins, antibodies, antigens, sugars and other carbohydrates, and the like. Moreover, the biological ligand may comprise a member of any specific or non-specific binding pair, such as either member of the following exemplary list: antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, repressor/inducer, or the like.

Non-biological ligands of the present invention include synthetic polymers and plastics which are known in the art.

Ligands, both biological and non-biological, may be cytophilic, that is, adapted to promote cell adhesion or cell attraction to the ligand. Cells that adhere to these ligands may be whole or fractionated cells. Such ligands may be extracellular matrix proteins, fibronectin, collagen, laminin, serum albumin, polygalactose, sialic acid, and various lectin binding sugars. Ligands may also be "biophilic," that is, may adhere or attract certain biological molecules or compounds. These ligand include antibodies or fragments of antibodies and their antigens, cell surface receptors and their ligands, nucleic acid sequences and many others that are known to those of ordinary skill in the art.

In practicing the present invention, the stamp being used may be referred to as being "inked" by the ligands. In general, this "inking" means that the stamp comprises on its surface a plurality of ligands, by which is meant either more than one of a particular ligand (i.e., more than one molecule of a ligand), or a variety of different ligands (e.g., molecules of different species, such as a protein and a small biological molecule). In other words, the stamp surface may comprise a heterogenous mixture or a homogenous sample of ligand. The stamp may be inked with a solution comprising the ligands that will be adsorbed to the stamp. Accordingly, the inking may, for example, be accomplished by (1) contacting the stamp with a material (i.e., paper, sponge) moistened with the ink, (2) pouring the ink directly onto the stamp, (3) applying the ink to the stamp with a an appropriate application device (e.g., a cotton swab, brush, sprayer, syringe, etc.), or (4) dipping the stamp surface into the solution. The ink may be allowed to dry on the stamp or may be blown dry. The inked stamp is then placed into contact with the functionalized polymer surface for a length of time deficient for the reactive moieties of the polymer surface and the ligand to bond covalently. The period of time for this will of course vary with the ligands, reactive moieties and polymers being used, but which will be able to be determined by one skilled in the art. For example, contacting the stamping surface with the surface polymer for a period of time of approximately 10 minutes is generally adequate to effect sufficient transfer, but contact may be maintained for longer or shorter periods of time if necessary or appropriate.

Once the stamp inked with the ligand is contacted to the polymer surface for a time sufficient to allow the covalent bonding of the reactive moieties of the polymer surface to the reactive moieties of the ligand, the stamp is then separated or removed from the polymer surface, leaving the ligand covalently bound to the functionalized polymer surface. The ligands bound to the polymer surface may, if be desired, be treated or modified further by chemical or thermal treatments known in the art. Additionally, if a reactive moiety located on the ligand remains exposed and available to binding by another ligand, such an additional ligand (a "second ligand") may be contacted to the ligand bound to the polymer surface. For example, if the ligand bound to the polymer surface is biotin or biotin-amine, then streptavidin, known to bind to biotin, may be contacted with the bound biotin to form a binding pair. If the ligand is a receptor, a putative receptor agonist or antagonist may be contacted to the polymer surface to determine if the agonist or antagonist compound binds to the receptor. If the ligand is an antibody bound to the polymer surface, the second ligand may be an antigen or hapten.

A polymer surface of the present invention may be stamped more than one time according to methods of the invention. Stamps subsequent to the first stamp may be the first stamp "re-inked," different stamps, stamps with different patterns thereon, and stamps comprising different ligands on the stamp surface.

Although useful in patterning methods (i.e., wherein the stamp contains one or more indentations to produce a pattern of bound ligands on the polymer surface), it is to be understood that the stamp may not have indentations on it. In other words, use of the stamp may create an uninterrupted "lawn" or "block" of ligands covalently bound to the surface of the polymer.

Devices that comprise polymer surfaces microstamped by the methods of the present invention are thus also an aspect of the invention. As will be apparent to those of ordinary skill in the art, the direct binding of biological and other ligands to polymers is important in many areas of biotechnology including, for example, production, storage and delivery of pharmaceutical proteins, purification of proteins by chromatography, design of biosensors and prosthetic devices, and production of supports for attached tissue culture The present method finds use in creating devices for adhering cells and other biological molecules into specific and predetermined positions. Accordingly, one example of a device of the present invention is a tissue culture plate comprising at least one surface microstamped by the method of the present invention. Such a device could be used in a method for culturing cells on a surface or in a medium and also for performing cytometry. Furthermore, the device could be used in immobilization of cells at a surface and for controlling the shape of a cell. Such devices are useful in a wide array of cellular biology applications, including cell culturing, recombinant protein production, cytometry, toxicology, cell screening, microinjection, immobilization of cells, influencing the state of differentiation of a cell including promoting differentiation, arresting differentiation or causing dedifferentiation. The devices of the invention also can be used to promote ordered cell-cell contact or to bring cells close to one another, but prevent such contact. The devices of the invention also are useful in the creation of artificial tissues for research or in vivo purposes and in connection with creating artificial organs such as artificial liver devices. The devices may also be useful in connection with generating surfaces for prosthetic or implantable devices.

The following Examples are provided to illustrate the present invention, and should not be construed as limiting thereof.

OVERVIEW OF EXAMPLES

In the following Examples, the present invention is illustrated by patterning biotin onto the polymer PET. The skilled artisan will appreciate that the present method is in no way limited to the use of biotin and PET. PET was chosen for illustrative purposes because it is a widely used biomaterial in synthetic vascular grafts and tissue culture. (Zdrahala, R. J. *J. Biomater. Appl.* 1996, 10, 309. Shakesheff, K.; Cannizzaro, S.; Langer, R. *J. Biomater. Sci., Polym. Ed.* 1998, 9, 507. Cima, L. G. *J. Cell. Biochem.* 1994, 56, 155. Massia, S. P.; Hubbell, J. A. *J. Biomed. Mater. Res.* 1991, 25, 223). Carboxylic acid groups are utilized as the illustrative active group on the polymer surface because they are a convenient functional group for conjugation to a wide variety of biomolecules. (Hermanson, G. T. Bioconjugate Techniques, Academic Press, $1^{st}$ Ed., San Diego, 1996). The choice of biotin as the biological ligand was dictated by the following reasons: (1) biotin is a prototypical small molecule biological ligand; (2) molecular recognition between biotin and streptavidin (or its homologue, avidin) is characterized by tight noncovalent interaction (equilibrium constant=$10^{13}$–$10^{15}$ $M^{-1}$), (Green, N. M. *Biochem. J.* 1966, 101, 774. Chilkoti, A.; Tan, P. H.; Stayton, P. S *Proc. Natl. Acad. Sci., USA* 1995, 92, 1754. Chilkoti, A.; Stayton, P. S. *J. Am. Chem. Soc.* 1995, 117, 10622. Wilchek, M.; Bayer, E. Avidin-Biotin Technology, Methods in Enzymology, Vol. 184, Academic Press: San Diego, 1990; Vol. 184) and therefore permits facile patterning of streptavidin onto a biotin pattern; and (3) the homotetrameric structure of streptavidin displays 222 point symmetry, (Weber, P. C.; Ohlendorf, D. H.; Wendoloski, J. J.; Salemme. F. R. *Science* 1989, 243, 85. Hendrickson, W. A.; Pahler, A.; Smith, J. L.; Satow, Y.; Merritt, E. A.; Phizackerley. R. P. *Proc. Natl. Acad. Sci.* (*USA*) 1989, 86, 2190) which positions two pairs of biotin binding sites on opposite faces of the protein, and thereby enables other biotinylated biomolecules (e.g., peptides, DNA, or other proteins) to be specifically immobilized onto the streptavidin pattern in a subsequent incubation step.

EXAMPLE 1

Materials and Methods; Surface Derivatization and Micropatterning

Poly(ethylene terephthalate) films (PET, Melinex® 442/300, Dupont) were cleaned in hexane and acetone and dried under nitrogen. The cleaned PET films were hydroxylated by immersion in 18.5% (v/v) formaldehyde/1 M acetic acid for 4 h. at room temperature. (Massia, S. P.; Hubbell, J. A. *Ann. N.Y. Acad. Sci.-Biomed. Engr.* 1990, 589, 261). Subsequently, the films were reacted with 1 M bromoacetic acid/2 M NaOH overnight, to convert the hydroxyl groups to carboxylic acid on the PET surface (PET-COOH). (Lofas, S.; Johnsson., B. *J. Chem. Soc., Chem. Commun.* 1990, 1526). The PET films were activated by immersion in an ethanol solution of 1-ethyl-3-(dimethylamino) propylcarbodiimide (EDAC, 0.1 M) and pentafluorophenol (PFP, 0.2 M) for 15 min. (Adamczyk, M.; Fishpaugh, J. R.; Mattingly, P. G. *Tetrahedron Lett.* 1995, 36, 8345. Kovacs, J.; Mayers, G. L.; Johnson, R. H.; Cover, R. E.; Ghatak, U. R. *J. Org. Chem.* 1970, 35, 1810).

The masters used to cast the poly(dimethylsiloxane) (PDMS) stamps were fabricated on polished Si wafers using AZ P4620 photoresist (Clariant, Inc.), which was spin coated to a thickness of ~5 microns and processed by contact photolithography. Elastomeric stamps were fabricated by casting PDMS against the photoresist on silicon masters with feature sizes of 10 μm or 40 μm squares, (Wilbur, J. L.; Kumar, A.; Kim, E.; Whitesides, G. M. *Adv. Mater.* 1994, 6, 600) and were subsequently oxidized in an air plasma (150 mtorr, 40 W, 1 min.) in a plasma reactor (Plasmod™, March Instruments Inc., Concord, Calif.), prior to use.

The ligand (+)-biotinyl-3-6,9, -trioxaundecanediamine (Pierce, hereafter referred to as biotin-amine) was printed by contacting a plasma-oxidized PDMS stamp, inked with 10 mM biotin-amine in ethanol, with the activated PET-COOH substrate for 10 min. Flat, plasma oxidized PDMS stamps were used to print biotin-amine for spectroscopic analysis by XPS and TOF-SIMS. Unreacted pentafluorophenyl esters were inactivated by reaction with 2-(2-aminoethoxy)ethanol (AEE, 10 mM, 0.1 M sodium bicarbonate, pH 8.3) for 20 min. The samples were cleaned with ethanol in an ultrasonic bath for 5 min., rinsed with distilled water, and dried, prior to spectroscopic analysis.

After printing biotin-amine on PET-COOH with a PDMS stamp, the substrate was incubated with 0.1 μM Alexa™ 488-labeled streptavidin in HEPES buffered saline (HBS, pH 7.4) containing 0.1% (w/v) BSA and 0.02% (v/v) Tween 20 detergent for one hour.

EXAMPLE 2

Summary of Methods of Analysis of Micropatterning

Because no single analytical technique is capable of elucidating the surface chemistry of micropatterned, derivatized polymers, we have interrogated each step in MAPS by a suite of complementary analytical techniques. The primary analytical technique that we used, time-of-flight secondary ion mass spectrometry (TOF-SIMS) is one of the few, currently available surface analysis techniques that enables spatially-resolved molecular characterization of micropatterned substrates. This is because TOF-SIMS provides a mass spectrum of the top 10–30 Å with high mass resolution and submicron lateral resolution. (Van Vaeck, L.; Adriaens, A.; Gijbels, R. *Mass Spectrom. Rev.* 1999, 18, 1. Benninghoven, A., *Angew. Chem. Intl. Ed.* 1994, 33, 1023. Pacholski, M. L., Winograd, N. *Chem. Rev.*, 1999, 99, 2977. Briggs, D. In *Polymer Surface Characterization by XPS and SIMS. Characterization of Solid Polymers*; S. J. Spells, Ed. Chapman & Hall: London, 1994; p.312).

In concert, spectroscopic studies of functionalized polymer surfaces by X-ray photoelectron spectroscopy (XPS) provides the elemental composition (Briggs, D. In *Polymer Surface Characterization by XPS and SIMS. Characterization of Solid Polymers*; S. J. Spells, Ed. Chapman & Hall: London, 1994; p. 312. Swingle II, R. S. *CRC Crit. Rev. Anal. Chem.* 1975, 5, 267. Carlson, T. A. *Photoelectron and Auger Spectroscopy*; Plenum Press: New York, 1975. Andrade, J. D. In X-ray Photoelectron Spectroscopy (XPS). Surface and Interfacial Aspects of Biomedical Polymers. 1. Surface Chemistry and Physics J. D. Andrade, Ed.; Plenum Press: New York, 1985; p. 105. Briggs, D. and Seah, M. P. Practical Surface Analysis, John Wiley & Sons: Chichester, 1983) as well as the concentration of functional groups from high resolution core level spectra (Ratner, B. D.; Castner D. G. *Coll. Surf. B: Biointerfaces*, 1994, 2, 333. Clark, D. T.; Harrison, A. *J. Poly. Sci., Polym. Chem. Ed.*, 1981,19, 1945–1955. Clark, D. T.; Thomas H. R. *J. Poly. Sci.: Poly. Chem. Ed*, 1978, 16, 791–820. Dilks, A. In *X-ray Photoelectron Spectroscopy for the Investigation of polymeric Materials. Electron Spectroscopy—Theory, Techniques and Applications*. Brundle, C. R Baker, A. D. Eds.; Academic Press: London, 1981, p. 277) and by complementary chemical derivatization methods. (Chilkoti, A.; Ratner, B. D. *In Surface Characterization of Advanced polymers*, Sabbatini, L., Zambonin, P. G., Eds.; VCH: Weinheim, 1993; p. 221). We also used fluorescence microscopy because it enables optical imaging of fluorophore-labeled proteins on micropatterned polymers with good contrast and lateral resolution of a few microns. Accordingly, confocal fluorescence microscopy and TOF-SIMS imaging was used to examine the formation of streptavidin micropatterns on the polymer surface described in Example 1.

EXAMPLE 3

Materials and Methods: X-ray Photoelectron Spectroscopy

XPS analysis was carried out on a SAX-100 spectrometer (Surface Science Incorporated, Mountain View, Calif.), equipped with a monochromatic AlK$_\alpha$ X-ray source, a hemispherical electron analyzer, and a low energy electron flood gun for charge compensation of insulators. Samples were typically introduced into a preparation chamber, which was maintained at a pressure of $10^{-4}$ torr, and then transferred into the analysis chamber, which was typically maintained at $10^{-8}$ torr. The samples were analyzed at either 15° or 55° take-off angle, defined as the angle between the sample plane and the hemispherical analyzer. The typical X-ray spot size was ~600 µm. Survey scan spectra were acquired from 0–1000 eV for elemental composition, and high-resolution spectra of the C$_{1s}$ core level were acquired from 278–300 eV.

EXAMPLE 4

Materials and Methods: Time-of-flight Secondary Ion Mass Spectrometry

TOF-SIMS spectra and images were obtained on a TRIFT II TOF-SIMS instrument (Physical Electronics, Eden Prairie Minn.). A mass-filtered $^{69}$Ga$^+$ liquid-metal primary ion gun was used with a current of ~600 pA. For spectral acquisition, the gun was operated at 15 keV and a pulse width of 12 ns. For imaging, the gun was operated at 25 keV and a pulse width of 30 ns. Details of the spectrometer are described elsewhere. (Schueler, B. *Microsc. Microanal. Microstruct.* 1992, 3, 119–139). The data was acquired over a mass range of m/z 0–1500. The data was collected using an ion dose below the static SIMS limit of $10^{13}$ ions/cm$^2$. A low energy electron beam was used for charge compensation.

EXAMPLE 5

Materials and Methods: Fluorescence Microscopy

Fluorescence microscopy of Alexa™ 488 labeled streptavidin patterns was performed on a BioRad MRC 1000 confocal microscope (BioRad Microscience Ltd., Hemel Hempstead, U.K.) with a 10× or 20× objective. The confocal microscope was operated at 10% power level and with a detector gain of 1500 V.

EXAMPLE 6

Results and Discussion: Surface Derivatization of PET

Figure 2:
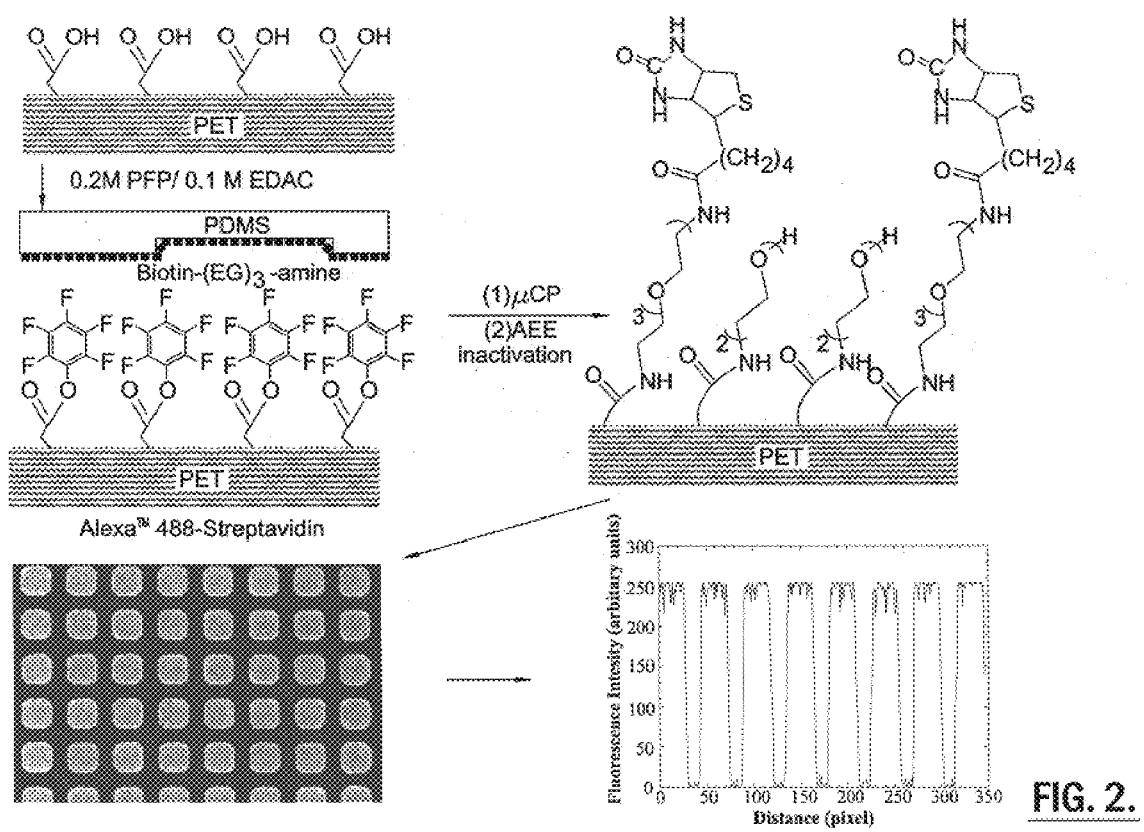
FIG. 2 is a schematic of the method of the present invention used to micropattern biotin-amine onto PET. The lower left panel is a 20×magnification confocal image of Alexa™ 488-labeled streptavidin (0.1 $\mu$M in HBS, pH 7.4) bound to biotin-amine, which was patterned onto PET-COOH using techniques described herein. A line profile of fluorescence intensity of Alexa™ 488-labeled streptavidin bound to biotin-amine patterns created by MAPS on PET-COOH is shown on its right.

PET was derivatized in two steps to introduce carboxylic acid groups at the surface, as shown in FIG. 1. The first step, the hydroxymethylation of the aromatic ring in PET introduced a benzylic hydroxyl group within the PET repeat unit, (Massia, S. P.; Hubbell, J. A. *Ann. N.Y. Acad Sci.-Biomed. Engr.* 1990, 589, 261) which was then converted to a carboxyl group by reaction with bromoacetic acid. (Lofas, S.; Johnsson., B. *J. Chem. Soc., Chem. Commun.* 1990, 1526). After the introduction of carboxylic acid groups on the surface of PET (the carboxyl derivatized PET surface is termed PET-COOH), the carboxylic acid groups were then activated by reaction with PFP (FIG. 2). We chose PFP to activate the carboxylic acid groups in PET-COOH, because previous reports suggest that pentafluorephenyl esters are significantly more reactive than the more commonly used N-hydroxysuccinimide ester. (Adamczyk, M.; Fishpaugh, J. R.; Mattingly, P. G. *Tetrahedron Lett.* 1995, 36, 8345. Kovacs, J.; Mayers, G. L.; Johnson, R. H.; Cover, R. E.; Ghatak, U. R. *J. Org. Chem.* 1970, 35, 1810) The activated PET surface was then patterned with biotin-amine by spatially-resolved reagent transfer using a PDMS stamp inked with the ligand (FIG. 2). Unreacted esters were quenched by reaction with AEE.

EXAMPLE 7

Results and Discussion: XPS Characterization

The carboxylation of PET was confirmed by XPS in combination with chemical derivatization with PFP. (Chilkoti, A.; Ratner, B. D. In *Surface Characterization of Advanced polymers*, Sabbatini, L., Zambonin, P. G., Eds.; VCH: Weinheim, 1993; p. 221). No fluorine was observed in unmodified PET after exposure to PFP/EDAC (Table 1). In contrast, 3–4 (atomic) % F was measured for PET-COOH derivatized with PFP. These results suggest that PET was successfully Functionalized with COOH groups. The Functionalization of PET with COOH groups proceeded homogeneously within the top 50 Å of the surface because XPS analyses at two different take off angles, 15° and 55° gave experimentally indistinguishable results. Furthermore, the measured F/C ratio for PFP-derivatized PET-COOH indicates that the carboxylic acid concentration in PET-COOH is ~21% of the theoretical maximum, which was calculated with the following assumptions: (1) 100% carboxylation of PET within the XPS sampling depth via the reaction scheme shown in FIG. 1, and (2) 100% derivatization of the carboxyl groups in PET-COOH by PFP/EDAC. With the above assumptions, the XPS results indicate that ~1 COOH group was introduced every 5 repeat units of PET.

TABLE I

Measured and calculated atomic ratios of PFP-derivatized PET-COOH and biotin-derivatized PET-COOH.

| Sample | Derivatization | Measured | | | [1]Calculated | | |
|---|---|---|---|---|---|---|---|
|  |  | N/C | O/C | F/C | N/C | O/C | F/C |
| PET | — | 0 | 0.31 | 0 | 0 | 0.40 | 0 |
| PET | 0.1 M PFP/ 0.2 M EDAC | 0 | 0.32 | 0 | 0 | 0.40 | 0 |
| PET-COOH | 0.1 M PFP/ 0.2 M EDAC | 0 | 0.33 | 0.06 | 0 | 0.37 | 0.26 |
| PET-biotin (solution) | Biotin-amine | 0.023 | 0.33 | 0 | 0.13 | 0.36 | 0 |
| PET-biotin (flat stamp) | Biotin-amine | 0.027 | 0.34 | 0 | 0.13 | 0.36 | 0 |

[1]The calculated atomic ratios assume the following: (1) the hydroxylation of PET proceeds specifically by hydroxymethylation of the aromatic ring in PET as shown in the reaction scheme in FIG. 1A with 100% yield; (2) all subsequent derivatization reactions also proceed with 100% yield throughout the entire sampling depth of XPS.

XPS of PET-COOH, derivatized with biotin-amine using a flat, plasma-oxidized PDMS stamp inked with ligand, provided direct evidence for the reaction of COOH groups on the surface of PET-COOH with biotin-amine. The N/C ratio of 0.023 for PET-COOH derivatized with biotin-amine using a flat PDMS stamp compares favorably with the N/C ratio of 0.027, obtained for derivatization of PET-COOH with biotin-amine from solution. In contrast, no nitrogen was detected on the surface of unmodified PET. These atomic ratios are ~19% of the theoretical maximum of 0.12. Upon correcting for the experimentally determined concentration of available COOH groups, these results also suggest that reaction of the available COOH groups present in PET-COOH with biotin-amine, after activation with PFP/EDAC, proceeded to completion.

The XPS $C_{1s}$ spectra of biotin-derivatized PET-COOH and native PET also corroborate these results. The $C_{1s}$ spectra of PET, acquired at various stages of the multistep functionalization procedure, were fit with the following criteria: (1) all spectra were corrected for sample charging using the $CH_x$ component in the resolved spectra at 284.6 eV as reference. Additional peaks for the oxygen-containing functionalities (Clark, D. T.; Harrison, A. J. *Poly. Sci., Polym. Chem. Ed.*, 1981, 19, 1945–1955. Clark, D. T.; Thomas H. R. *J. Poly. Sci.: Poly. Chem. Ed.*, 1978, 16, 791–820. Dilks, A. In *X-ray Photoelectron Spectroscopy for the Investigation of Polymeric Materials. Electron Spectroscopy—Theory, Techniques and Applications.* Brundle, C. R Baker, A. D. Eds.; Academic Press: London, 1981, p.277) were incorporated in the peak fit: these include C—O—H/R (286.2 eV), COOR (288.6 eV) and a →*shakeup satellite at 291.6 ev.(Gardella, J. A.; Ferguson, S. A.; Chin, R. L. *Appl. Spectrosc.* 1986, 40, 224). Full widths at half maximum of the component peaks in the spectral envelope were constrained to 1.2–1.4 eV during curve fitting, which is consistent with the energy resolution of the SAX-100 spectrometer.

The $C_{1s}$ spectra of PET PET-OH, and PET COOH (Table II) were qualitatively very similar, which is due to the low level of functionalization of PET, and the high concentration of COOR groups that are present in native PET, which mask the incorporation of carboxyl groups in PET-COOH. The spectrum of native PET (and PET-OH and PET-COOH) were fit with four peaks, which were assigned to $CH_x$, C—O—R, COOR and a →*shakeup satellite. The peak area ratio of 3.3: 1: 0.9 for the $CH_x$: C—O—R: COOR species, determined by curve fitting of the $C_{1s}$ spectrum of PET is close to the stoichiometric 3:1:1 ratio of PET.

TABLE II

Resolved XPS high resolution $C_{1S}$ spectra. Details of the peak fit are in the text.

| Sample | % $CH_x$ (284.6 eV) | % C-N/ C-S (285.4 eV) | % C-O-R (286.2 eV) | % COOR (288.6 eV) | % -> * (291.6 eV) |
|---|---|---|---|---|---|
| PET | 62.7 | — | 18.7 | 16.7 | 1.9 |
| PET-OH | 61.7 | — | 18.8 | 16.5 | 2.0 |
| PET-COOH | 62 | — | 18.9 | 16.5 | 2.5 |
| PET-biotin (flat stamp) | 48.6 | 12.6 | 18.6 | 16.4 | 1.9 |

The reaction of biotin-amine with PET-COOH clearly alters the $C_{1s}$ (Table II). Curve fitting of the spectrum of biotin-derivatized PET-COOH by the above criteria required the inclusion of a new peak, centered at 285.4 eV. This peak was assigned to the C—N and C—S species in biotin. (Beamson, G.; Briggs, D. *High resolution XPS of organic polymers*, John Wiley: Chichester, 1992). Assuming homogeneous functionalization within the XPS sampling depth, the (C—S +C—N): $CH_x$ ratio of 0.23 for PET-COOH derivatized with amine-terminated using a flat stamp inked with the ligand suggests that ~1 biotin molecule is introduced into every 5 repeat units in PET, which corroborate the results obtained from XPS elemental analysis.

EXAMPLE 8

Results and Discussion: Fluorescence Microscopy

The spatial distribution of streptavidin on the micropatterned biotin on PET-COOH was examined by incubating the patterned substrate with Alexa-488 labeled streptavidin. A 20×magnification confocal image of Alexa™ 488-labeled streptavidin (FIG. 2, lower left panel) shows that streptavidin is spatially-localized on the periodic, 40 μm×40 μm biotin micropattern printed by MAPS on PET-COOH. The average contrast ratio of the protein pattern in this image is 250:1 (FIG. 2, line intensity profile), and clearly demonstrates the successful localization of streptavidin on the biotin pattern, mediated by molecular recognition between the protein and immobilized ligand, as well as suppression of streptavidin adsorption on the unstamped regions, due to the presence of BSA and Tween 20™.

In contrast, the fluorescence intensity of unmodified PET, which was similarly stamped with a plasma-oxidized PDMS stamp inked with biotin-amine, followed by incubation with Alexa™ 488-labeled streptavidin showed an average contrast ratio between the patterned region and background of ~40:1 (results not shown). These results suggest that the covalent incorporation of biotin into PET-COOH provides a six fold higher concentration of immobilized streptavidin at the surface as compared to adsorption of biotin. There are at least two possible reasons for the low, albeit significant streptavidin adsorption on the control, unmodified PET stamped with biotin-amine: (1) streptavidin bound to adsorbed biotin, which was incompletely desorbed during the rinsing procedure that preceded incubation with Alexa™ 488-labeled streptavidin; (2) the different surface chemistry between stamped and unstamped regions, due to the presence of residual biotin and PDMS transferred from the stamp, resulted in greater adsorption of streptavidin to the regions that were in contact with the PDMS stamp as compared to the background.

Figure 3A:
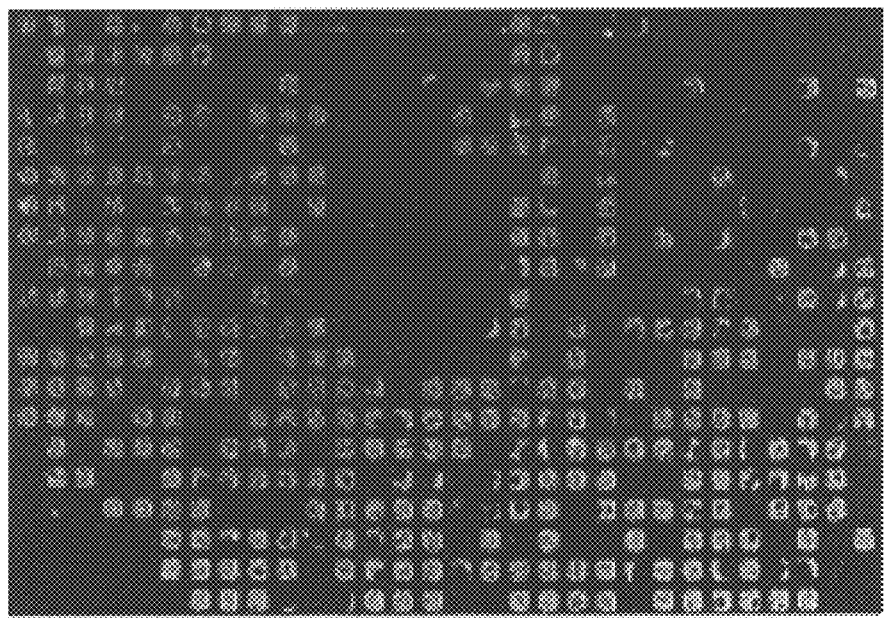
FIG. 3 is of fluorescence images of Alexa™ 488-strepatvidin bound to biotin micropatterns fabricated on PET using an unoxidized PDMS stamp versus a PDMS stamp oxidized by a 1 min. air plasma treatment.
Figure 3B:
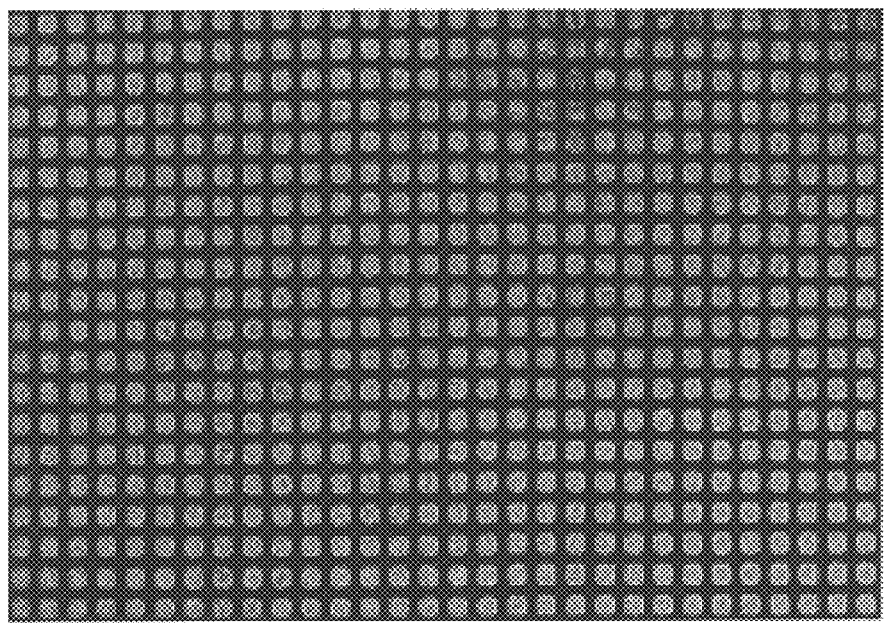

The quality of the biotin micropattern printed by MAPS was strongly affected by the surface energy of the PDMS stamp. Untreated PDMS stamps produced poor quality patterns, as shown by fluorescence microscopy of the binding of Alexa-labeled streptavidin (FIG. 3A). In contrast, a 1 min. air plasma treatment substantially improved the transfer of ligand to the surface (FIG. 3B), presumably because the increased hydrophilicity of the plasma-oxidized PDMS surface enabled complete wetting of the surface of the PDMS stamp by the ligand solution. This result is consistent with that of Lahiri et al.(supra) for reactive μCP of biotin on SAMs on gold.

We also examined the reproducibility of the biotin micropattern, by stamping a large (9 mm×9 mm) area of PET-COOH with biotin-amine using a stamp with 10 μm square features and an interfeature spacing of 5 μm. The patterns were incubated with Alexa 488-labeled streptavidin and visualized by fluorescence microscopy. FIG. 4, a composite 10×image, obtained from different regions of the substrate, shows the uniformity of the pattern over the entire, stamped region. The loss of feature resolution and intensity, observed at the edge of the stamped regions, is probably caused by edge effects due to inhomogeneous distribution of the applied stress on the PDMS stamp and slight curvature of the substrate. The stability of the streptavidin pattern was also examined; after fluorescence imaging, the sample was stored in HBS (pH 7.4) containing Alexa™ 488-labeled streptavidin (0.1 μM) for a week, and then examined again by fluorescence microscopy. No differences were observed either in the total intensity of the patterned regions with time or in the contrast between patterned regions and background (results not shown).

EXAMPLE 9

Results and Discussion: TOF-SIMS Spectroscopy

Figure 5:
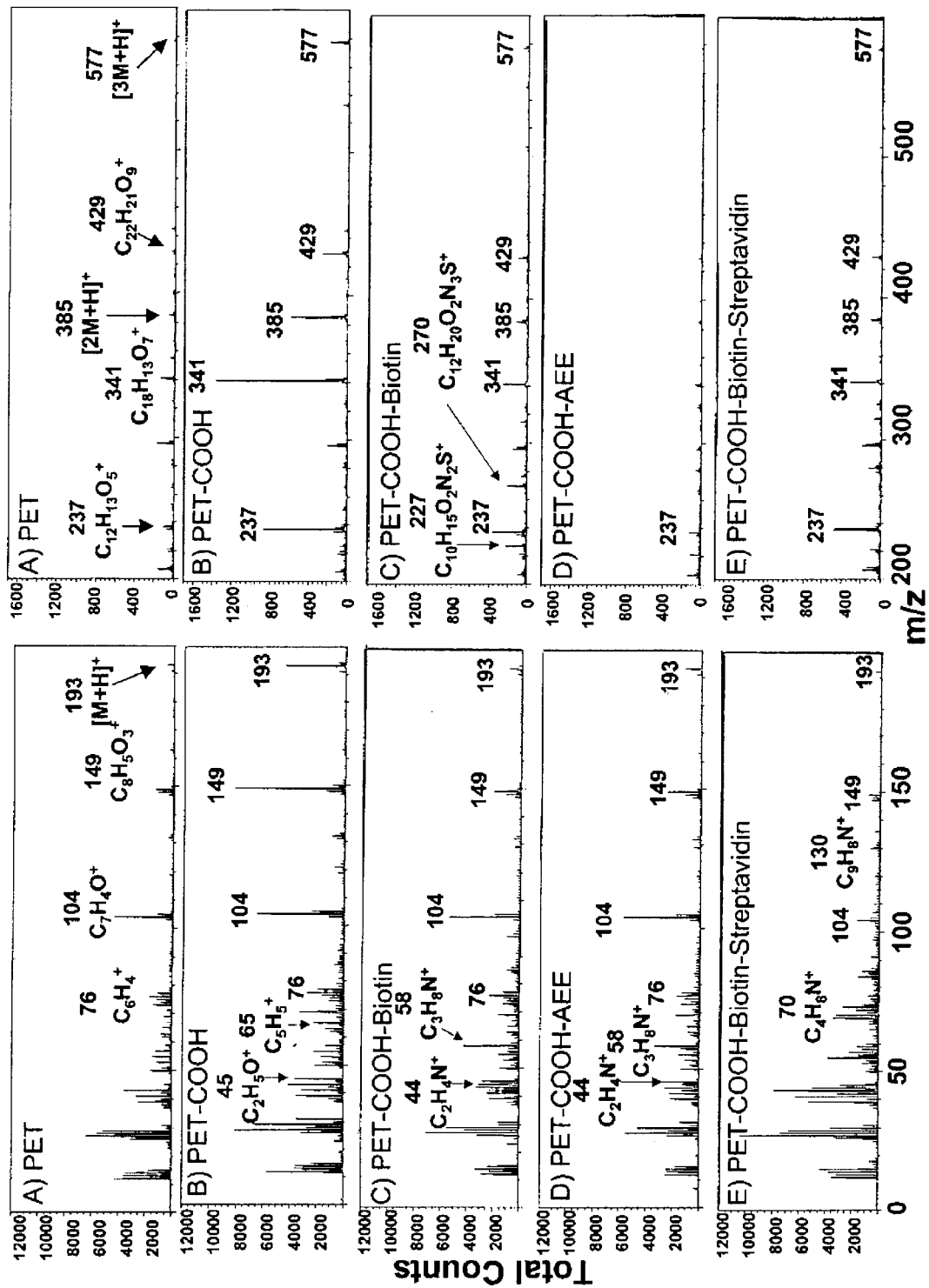
FIG. 5 is (+) TOF-SIMS spectra of: PET (A); PET-COOH (B); PET-COOH derivatized with biotin-amine (C), PET-COOH derivatized with AEE (D), and PET-COOH derivatized with biotin-amine and incubated with streptavidin (E). Each modification step was confirmed by the presence of molecular ions unique for each molecule. P represents characteristic PET ions (M=repeat unit of PET). B represents characteristic biotin ions. A represents characteristic AEE ions. S represents characteristic streptavidin ions.

In order to monitor each step of the functionalization of PET by MAPS, it was necessary to first identify secondary ions that are unique to each step of the derivatization procedure. Samples were prepared for each derivatization step and analyzed by TOF-SIMS. The positive ion spectrum of native PET shows characteristic peaks for PET at m/z 76, 104, 149, 193 [M+H]$^+$ (M=repeat unit of PET), 237, 341, 385 [2M +H]$^+$, 429, 577 [3M+H]$^+$ and 769 [4M+H]$^+$ (FIG. 5A). (The Static SIMS Library, Version 2, SurfaceSpectra Limited, Manchester, UK, 1999). The positive ion spectrum of PET-COOH is qualitatively similar to that of PET (FIG. 5B); the series of molecular secondary cations, characteristic of PET are also observed in the TOF-SIMS spectrum of this sample. The peaks at m/z 45 ($C_2H_5O^+$) and m/z 65 ($C_5H_5^+$), however, display increased intensity relative to unmodified PET. Furthermore, the intensity of molecular ions derived from PET increased by between five- and ten-fold for PET-COOH compared to native PET. This increase in intensity was observed both in positive (FIG. 5B) and negative ion mode (results not shown), suggesting an increased concentration of PET oligomers on the surface of the modified polymers. (Briggs, D. *Surf. Interface Anal.* 1986, 8, 133–136). We believe that the low MW PET oligomers are created by hydrolytic chain cleavage of PET, which also creates hydroxyl and carboxylic acid functionalities at the new chain ends. Therefore, the scheme shown in FIG. 1 is only approximate, and it is likely that a substantial fraction of reactive groups arise from side reactions such as hydrolytic cleavage of the PET backbone.

PET-COOH substrates were reacted with biotin-amine by conformal contact of a flat PDMS stamp, inked with the reagent, with the surface or by reaction from solution. TOF-SIMS provided evidence for the reaction of biotin with the COOH groups. FIG. 5C shows the TOF-SIMS positive ion spectrum PET-COOH reacted with biotin-amine from solution, where new peaks at m/z 44 ($C_2H_4N^+$) and 58 ($C_3H_8N^+$) are observed. Molecular ions of low intensity at m/z 227 ($C_{10}H_{15}O_2N_2S^+$) and 270 ($C_{12}H_{20}O_2N_3S^+$) are also observed. (The Static SIMS Library, Version 2, SurfaceSpectra Limited, Manchester, UK, 1999. Briggs, D. *Surf. Interface Anal.* 1986, 8, 133–136). These results strongly suggest the covalent reaction of biotin-amine with PET-COOH, because these peaks were not observed on native PET or PET-COOH, and biotin-amine was the only nitrogen containing species in this multi-step derivatization procedure. Further, the new peaks observed at m/z 26 ($CN^-$) and 42 ($CNO^-$) in the negative ion spectrum also indicate the introduction of a nitrogen-containing moiety (FIG. 6).

After derivatizing PET-COOH with biotin-amine using a patterned stamp in MAPS, the unpatterned regions were quenched with AEE. Therefore, it was necessary to analyze a control sample of AEE-modified PET-COOH to identify characteristic TOF-SIMS peaks for AEE. The positive ion spectrum is dominated by peaks that are characteristic of PET (FIG. 5D). Compared to the spectra of PET-COOH, the peaks at m/z 44 ($C_2H_4N^+$), 58 ($C_3H_8N^+$), 26 ($CN^-$) and 42 ($CNO^-$)(negative ions results are not shown) display significantly greater intensity. Unique peaks for AEE were not observed, compared to biotin-derivatized PET-COOH. The important distinction between the spectrum of PET-COOH derivatized with AEE compared to biotin-amine is the presence of the molecular biotin species (m/z 227$^+$ and 270$^+$) in the positive ion spectrum (FIG. 5C) and the greater intensity of m/z 26$^-$ and 42$^-$ in the negative ion spectrum of biotin-derivatized PET-COOH (FIG. 6).

Figure 6:
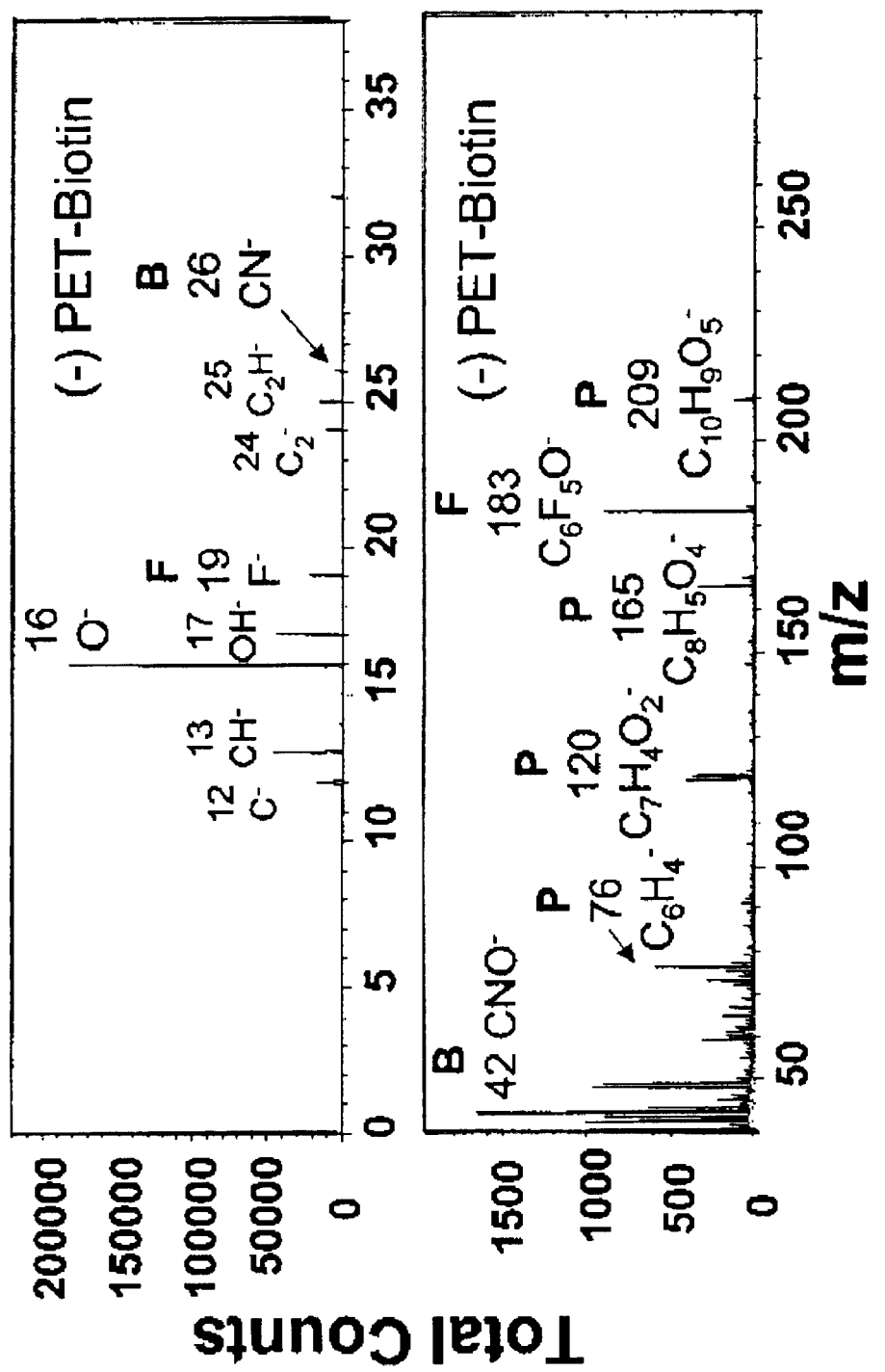
FIG. 6 is a (−) TOF-SIMS spectrum of PET-COOH reacted with biotin-amine. P represents characteristic PET ions. B represents characteristic biotin ions. F represents characteristic PFP ions. The presence of PFP species indicates the activating agent is not fully quenched in the derivatization reaction.

The negative ion TOF-SIMS spectrum of PET-COOH reacted with biotin-amine also shows evidence of PFP, which was used to convert carboxylic acid groups to reactive pentafluorophenyl esters (FIG. 6). The spectrum contains significant peaks at m/z 19 ($F^-$) and 183 ($C_6F_5O^-$), which is the intact parent ion of PFP. The presence of these ions suggest that the reaction of the pentafluorophenyl ester with AEE and subsequent hydrolysis of unreacted pentafluorophenyl ester in the unpatterned, background region only proceeded partially to completion.

In the final step of MAPS, the biotin-derivatized PET was incubated with Alexa488-labeled streptavidin to enable protein micropatterning via molecular recognition between biotin and streptavidin. The TOF-SIMS spectrum of this sample exhibited unique peaks for streptavidin at m/z=70 ($C_4H_8N^+$) and 130 ($C_9H_8N^+$) in the positive ion mode (FIG. 5E), and at m/z=46 ($NO_2^-$) and 62 ($NO_3^-$) in the negative ion mode (results not shown). Attribution of these ions to streptavidin was confirmed by TOF-SIMS of an adsorbed monolayer of Alexa 488 labeled streptavidin on PET (results not shown).

EXAMPLE 10

Results and Discussion: TOF-SIMS Imaging

The imaging mode of TOF-SIMS was used to analyze the patterned samples and monitor the distribution of characteristic molecular species. Patterned biotin samples were rinsed in an ultrasonic bath of ethanol, prior to analysis, to reduce PDMS contamination to background level.

Figure 7A:
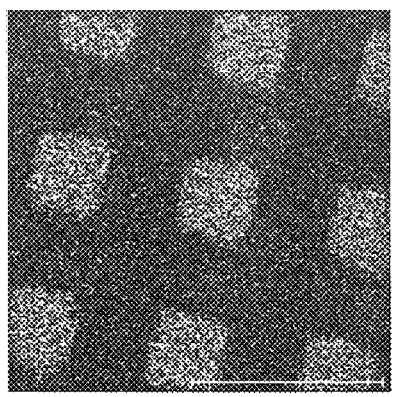
FIG. 7 is of TOF-SIMS images of a sample of biotin patterned onto activated PET using a 40 $\mu$m stamp. The map of the CN$^-$ ion (26 Da) in A confirms the presence of biotin created by the stamp. In B, the map of the $C_6F_5O^-$, the PFP molecular anion (m/z 183$^-$), shows that PFP is preferentially located in the unstamped regions. The map of the molecular ion (m/z 227$^+$) corresponds well with the CN$^-$ map (C). In D, the map of the m/z 104 molecular ion of PET indicates that PET is preferentially exposed in the unstamped regions. Images shown in the upper panels were acquired from the same area, and the other two images were acquired from different areas.

TOF-SIMS imaging of cleaned samples enabled spatial mapping of biotin-amine, patterned onto activated PET-COOH, using a PDMS stamp with 40 μm square features. The square regions of biotin were best observed by mapping the distribution of $CN^-$ in the negative ion mode. The image clearly indicates the biotin ligand is spatially localized in the 40 μm square contact regions (FIG. 7A). The $CN^-$ map displays significant intensity in the background, which arises from AEE, the reagent used to pentafluorophenyl ester groups not functionalized with biotin-amine. The visible contrast in the image is a consequence of the higher intensity of this peak from the biotinylated regions as compared to the background regions functionalized with AEE, and demonstrates that even the difference in peak intensity of an ion created from two different parent molecules on the surface is sufficient to spatially map the surface chemistry.

Figure 7B:
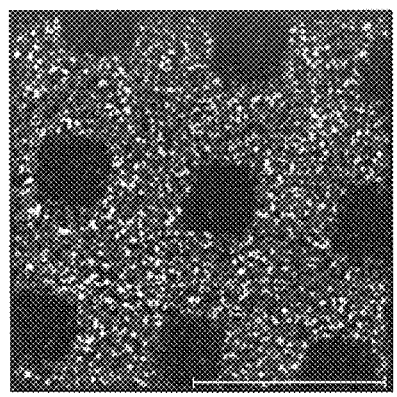
Figure 7C:
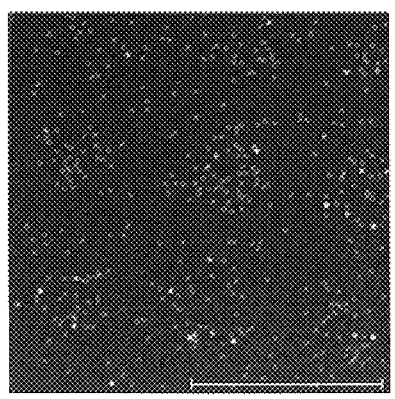

Although its intensity is very low, the peak at $227^+$, the parent molecular peak of biotin, can also be used to unequivocally map the distribution of biotin. Because the surface is destroyed over time by collision of the primary ion beam with the surface in TOF-SIMS, it is likely that the biotin molecule most likely fragmented before significant signal-to-noise could be obtained in the imaging mode of TOF-SIMS. The image of m/z $227^+$, nevertheless, even with poor signal to noise, demonstrates that biotin is localized in the 40 μm square regions (FIG. 7C).

PFP was used to activate the entire PET-COOH surface before stamping with biotin-amine. FIG. 7B shows the image of the parent molecular anion of PFP (m/z $183^-$) after patterning PFP derivatized PET-COOH with biotin-amine and quenching with AEE. The peak at m/z 183 is localized solely to the regions where biotin is absent, which suggests that reaction of PFP with biotin and AEE, and subsequent hydrolysis in buffer proceeds to completion in the patterned regions but is incomplete in the background.

Figure 7D:
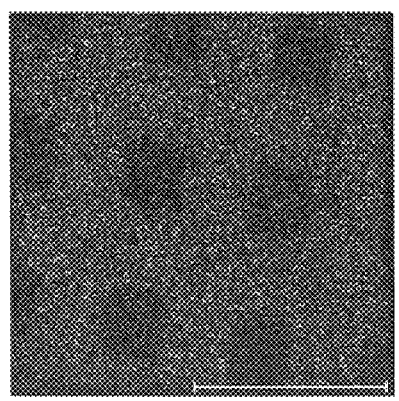

FIG. 7D shows the spatial distribution of m/z 104 ($C_7H_4O^+$), which is unique to PET, and shows that the intensity of this ion is highest in the regions that do not contain biotin. Because PET is the substrate, we believe the observed contrast is a consequence of the shallow sampling depth of TOF-SIMS for molecular ions,[68] so that biotin molecules in the patterned regions mask PET. In contrast, the PET signal is stronger from the background, because PFP and AEE are smaller molecules than biotin and may have a lower surface coverage.

Figure 8A:
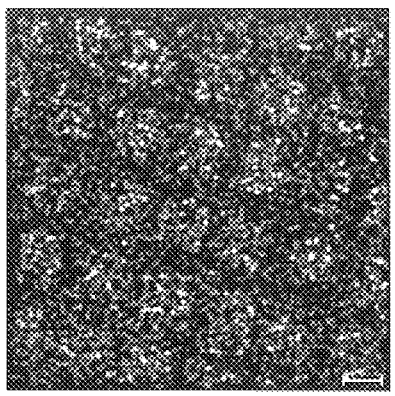
FIG. 8 is TOF-SIMS images of a streptavidin pattern. The PET-COOH substrate was first patterned with biotin-amine using a 10 $\mu$m stamp and subsequently incubated with streptavidin in the presence of Tween20™. A is the molecular map of m/z 104 ion ($C_7H_4O^+$) shows that PET is exposed in the unstamped regions. The characteristic streptavidin ion m/z 70 ion ($C_4H_8N^-$) in B shows that streptavidin binds preferentially to the stamped biotin pattern. C shows that residual Tween20™ is preferentially adsorbed to the unstamped regions.
Figure 8B:
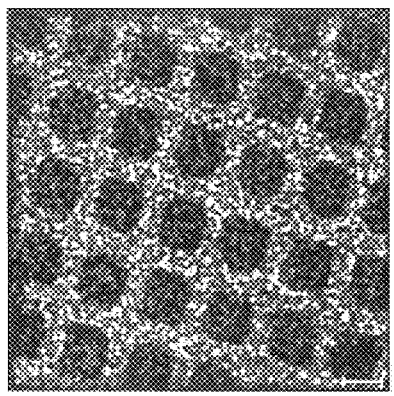
Figure 8C:
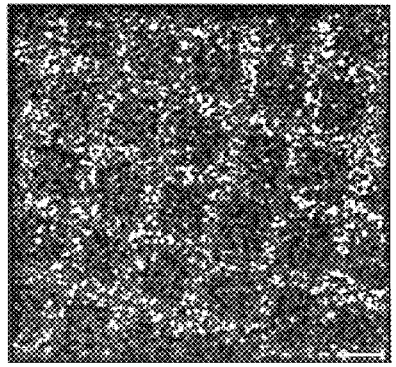

The patterned biotin samples were also analyzed by imaging TOF-SIMS after incubation with streptavidin (FIG. 8). The image of m/z 70, which is unique to streptavidin, shows the spatial localization of streptavidin and reveals that the streptavidin binds selectively to the 10 μm square patterned biotin regions (panel B). In contrast, the image of m/z 104 for PET, shows higher intensity for regions of PET substrate that were not in contact with the PDMS stamp (FIG. 8A). The two images show a contrast inversion and demonstrate the successful patterning of PET with streptavidin.

Figure 9A:
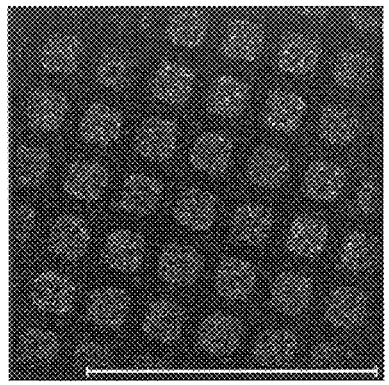
FIG. 9 illustrates the effect of Tween20™ blocking agent (BA) on binding of streptavidin to a biotin micropattern. TOF-SIMS images of micropatterned biotin on PET-COOH incubated with streptavidin were acquired with (A and B) and without Tween20™ (C and D) in the protein solution: A and C m/z 104 ($C_7H_4O^+$ ion from PET substrate); B and D m/z 26 (CN$^-$). The square 10 $\mu$m biotin pattern in images of A and B included Tween20™ in the streptavidin binding buffer, and show that streptavidin binds preferentially to the biotinylated regions with low nonspecific adsorption of protein to the background. In contrast, the square 40 $\mu$m biotin pattern in images shown in C and D did not include Tween20™ in the streptavidin solution, and show significant nonspecific adsorption of streptavidin to the patterned surface.
Figure 9B:
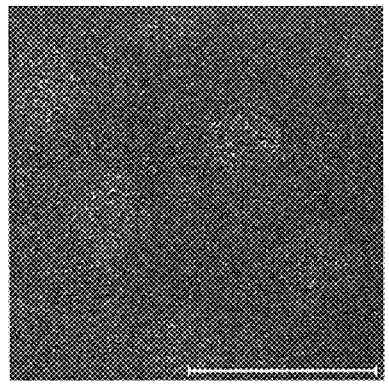
Figure 9C:
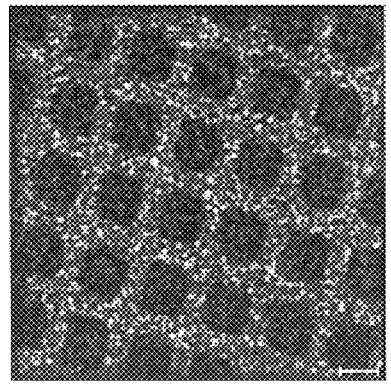
Figure 9D:
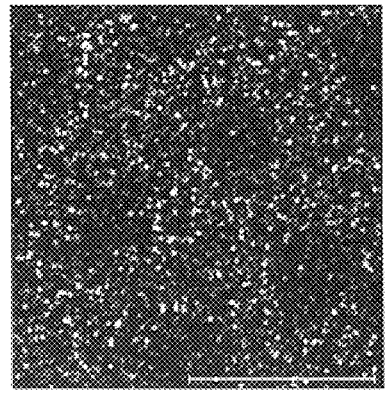

Streptavidin was incubated in the presence of Tween 20™, a blocking agent composed of polyoxyethylene sorbitan monostearate. TOF-SIMS clearly shows the presence of Tween2™ by the characteristic peaks at 227, 255 and 283 in the positive ion mode (panel C). These peaks represent the series of myristic, palmitic and stearic fatty acids, and are sidechains of the sorbitan molecule. (Beamson, G.; Briggs, D. *High resolution XPS of organic polymers*, John Wiley: Chichester, 1992). The TOF-SIMS image of this series of peaks shows that Tween 20™ is preferentially located in the background region. This localization of Tween 20™ also explains the high, 250:1 contrast observed for streptavidin in fluorescence microscopy. The high contrast of the fluorescence images can be attributed both to the selective binding of streptavidin to patterned biotin, as well as the preferential adsorption of the surfactant, Tween 20, to the background. In comparison, TOF-SIMS images of biotin-derivatized PET-COOH incubated with streptavidin without the addition of the Tween 20™, showed poor spatial resolution of protein-containing peaks. This is clearly seen upon comparing the m/z 26 map ($CN^-$) for a streptavidin pattern incubated with (FIG. 9, panel B) and without Tween 20 (FIG. 9D). Similarly, the contrast inversion of representative secondary ions from the PET substrate (m/z $104^+$) (FIG. 9, panel A), which is a consequence of the preferential binding of streptavidin to the biotin micropattern and the ~1–2 nm sampling depth of TOF-SIMS, is also substantially reduced when the blocking agent is not included (FIG. 9, panel C). These results clearly confirm that Tween 20 significantly reduces nonspecific adsorption of streptavidin to the background, unstamped regions.

Overall, the present MAPS invention finds advantage in that is applicable to a wide variety of polymers that are amenable to surface modification, and thus is useful for micron scale patterning of small molecule ligands, peptides, and protein onto polymer surfaces for biomaterial and biotechnological application. Micropatterning of reactive ligands on derivatized polymer substrates with a spatial resolution of at least 5 μM, high contrast and good reproducibility. MAPS will find particular use in the spatially-resolved immobilization of biomolecules that are difficult to stably adsorb onto polymers, such as small biological ligands.

The foregoing is illustrative of the present invention and is not to be construed as limiting thereof. The invention is defined by the following claims, with equivalents of the claims to be included therein.

That which is claimed is:

1. A method of microstamping a polymer surface with a biological ligand, comprising:

introducing a reactive moiety onto the polymer surface to provide a functionalized polymer surface, wherein said step of introducing a reactive moiety onto the polymer surface comprises at least one method selected from the group consisting of hydrolysis, reduction, photoinitiated graft polymerization, aminolysis, forming a surface interpenetrating network of poly(ethylene oxide), chemical reaction at hydroxyl end-groups, corona discharge, reactive plasma etching, laser treatment, and ion beam modification;

contacting the functionalized polymer surface having the first reactive moiety thereon with a stamp that has adsorbed onto its surface at least one biological ligand comprising a second reactive moiety, wherein the second reactive moiety of the biological ligand and the first reactive moiety of the functionalized polymer surface form a covalent bond; and then separating the stamp from the functionalized polymer surface, thereby leaving the biological ligand directly and covalently bound to the functionalized polymer surface.

2. The method of claim 1, wherein the ligand is selected from the group consisting of small biological molecules, proteins, peptides, and nucleic acids.

3. The method of claims 2, wherein the ligand is a small biological molecule.

4. The method of claims 2, wherein the ligand is a peptide.

5. The method of claims 2, wherein the ligand is a biotin.

6. The method of claims 2, wherein the ligand is a biological polymer.

7. The method of claim 1 wherein the first reactive moiety of the functionalized polymer surface is selected from the group consisting of amine groups, thiol groups, sulfide groups, disulfide groups, silane groups, chlorosilane groups, carboxylic acids, nitrite groups, isonitrile groups, hydroxamic acids, acid chlorides, anhydrides, sulfonyl groups, phosphoryl groups, azo groups, diazo groups and hydroxyl groups.

8. The method of claim 1, wherein the second reactive moiety of the biological ligand is selected from the group consisting of amine groups, thiol groups, sulfide groups, disulfide groups, silane groups, chlorosilane groups, carboxylic acids, nitrite groups, isonitrile groups, hydroxamic acids, acid chlorides, anhydrides, sulfonyl groups, phosphoryl groups, azo groups, diazo groups and hydroxyl groups.

9. The method of claim 1, wherein the polymer surface is the surface of a polymer selected from the group consisting of poly(ethylene terephthalate) (PET), polystyrene (PS), polycarbonate (PC), poly(epsilon-caprolactone) (PECL or PCL), poly(methyl methacrylate) (PMMA), poly(lactic acid) (PLA), polydimethylsiloxane (PDMS), polybutadiene (PB), polyvinylalcohol (PVA), fluorinated polyacrylate (PFOA), poly(ethylene-butylene) (PEB), and poly(styrene-acrylonitrile) (SAN).

10. The method of claim 1, wherein the polymer surface is the surface of poly(ethylene terephthalate) (PET).

11. The method of claim 1, wherein the polymer surface is functionalized prior to the contacting step by first introducing carboxylic acids onto the surface of the polymer, and then activating the carboxylic acids.

12. The method of claim 11, wherein the carboxylic acids are functionalized by activating the carboxylic acids to pentafluorophenyl esters.

13. The method of claims 1, wherein the polymer surface is fabricated as a flat surface.

14. The method of claim 1, wherein the polymer surface is fabricated as a curved surface.

15. The method of claim 1, wherein the stamp is an elastomeric stamp.

16. The method of claim 1, wherein the stamp is a poly(dimethylsiloxane) (PDMS) stamp.

17. The method of claim 1, wherein the stamp is plasma-oxidized prior to the contacting step.

18. The method of claim 1, wherein the stamp is chemically oxidized prior to the contacting step.

19. The method of claim 1, wherein a plurality of biological ligands are adsorbed on the stamp in a pattern, and wherein the pattern of biological ligands is covalently bound to the polymer surface after the separating step.

20. The method of claim 19, wherein the stamp comprises at least one indentation in the plurality of biological ligands bound to the stamp in a pattern.

21. The method of claim 1, wherein the biological ligand is cytophilic.

22. The method of claim 1, wherein the second reactive moiety of the biological ligand is linked to the biological ligand by a spacer.

23. The method of claim 22, wherein the spacer is an ethylene glycol oligomer.

24. The method of claim 1, further comprising binding a second ligand to the biological ligand covalently bound to the polymer surface after the separating step.

25. The method of claim 24, wherein the second ligand is streptavidin, and the biological ligand covalently bound to the polymer surface after the separating step is biotin.

26. method of forming a device comprising at least one microstamped polymer surface, wherein the polymer surface is covalently bound to at least one ligand, comprising:

introducing a reactive moiety onto the polymer surface of a device to provide a functionalized polymer surface, wherein said step of introducing a reactive moiety onto the polymer surface comprises at least one method selected from the group consisting of hydrolysis, reduction, photoinitiated graft polymerization, aminolysis, forming a surface interpenetrating network of poly(ethylene oxide), chemical reaction at hydroxyl end-groups, corona discharge, reactive plasma etching, laser treatment, and ion beam modification;

contacting the functionalized polymer surface with a stamp that has adsorbed onto its surface at least one biological ligand comprising a second reactive moiety that binds the first reactive moiety on the functionalized polymer surface, wherein the second reactive moiety of the biological ligand and the first reactive moiety of the functionalized polymer surface of the device form a covalent bond; and then separating the stamp from the at least one polymer whose surface is functionalized of the device, thereby leaving the biological ligand covalently and directly bound to the first reactive moiety on the polymer surface of the device.

27. The method according to claim 26, wherein the polymer surface of the device is a synthetic polymer surface.

28. The method according to claim 26, wherein the polymer surface of the device is a biological polymer surface.

29. The method according to claim 26, wherein the polymer surface of the device is a plastic polymer surface.

30. The method according to claim 26, wherein the biological ligand is cytophilic.

31. The method according to claim 26, wherein the stamp comprises a plurality of ligands adsorbed onto the surface of the stamp in a pattern, thereby leaving a plurality of ligands covalently bound to the functionalized polymer surface of the device in the pattern.

32. The method according to claim 26, herein the device is a tissue culture plate.

* * * * *